US007423178B2

(12) United States Patent
Oevering et al.

(10) Patent No.: US 7,423,178 B2
(45) Date of Patent: Sep. 9, 2008

(54) PROCESS FOR TREATING AN ORGANIC SOLUTION COMPRISING CYCLOHEXANONE OXIME, CYCLOHEXANONE, AND AN ORGANIC SOLVENT

(75) Inventors: Hendrik Oevering, Elsloo (NL); Arno H Benneker, Doenrade (NL); Johannes A L Brouwers, Echt (NL)

(73) Assignee: DSM IP Assets B.V., Heerlen (NL)

( * ) Notice: Subject to any disclaimer, the term of this patent is extended or adjusted under 35 U.S.C. 154(b) by 197 days.

(21) Appl. No.: 10/541,196

(22) PCT Filed: Jan. 28, 2004

(86) PCT No.: PCT/NL2004/000063

§ 371 (c)(1),
(2), (4) Date: Jun. 30, 2005

(87) PCT Pub. No.: WO2004/067497

PCT Pub. Date: Aug. 12, 2004

(65) Prior Publication Data

US 2006/0079678 A1    Apr. 13, 2006

(30) Foreign Application Priority Data

Jan. 30, 2003  (EP)  .................................. 03075336

(51) Int. Cl.
*C07C 249/08* (2006.01)
(52) U.S. Cl. ........................ 564/259; 564/267; 564/253
(58) Field of Classification Search ....................... None
See application file for complete search history.

(56) References Cited

FOREIGN PATENT DOCUMENTS

| EP | 0 005 291 | | 11/1979 |
|----|-----------|---|---------|
| EP | 0 550 965 A2 | * | 7/1993 |
| GB | 1138750 | | 1/1969 |
| WO | WO 01/94297 A1 | * | 12/2001 |

* cited by examiner

*Primary Examiner*—Yvonne Eyler
*Assistant Examiner*—Yevegeny Valenrod
(74) *Attorney, Agent, or Firm*—Nixon & Vanderhye P.C.

(57) ABSTRACT

The invention relates to a process for treating an organic solution comprising cyclohexanone oxime, cyclohexanone and an organic solvent, said process comprising distilling the organic solution such as to obtain (i) a first product comprising organic solvent, (ii) a second product comprising cyclohexanone and (iii) a third product comprising cyclohexanone oxime; and feeding the second product to a cyclohexanone oxime synthesis zone in which hydroxylammonium is reacted with cyclohexanone to form cyclohexanone oxime.

22 Claims, 1 Drawing Sheet

PROCESS FOR TREATING AN ORGANIC SOLUTION COMPRISING CYCLOHEXANONE OXIME, CYCLOHEXANONE, AND AN ORGANIC SOLVENT

This application is the US national phase of international application PCT/NL2004/000063 filed 28 Jan. 2004 which designated the U.S. and claims benefit of EP 03075336.2, dated 30 Jan. 2003, the entire content of which is hereby incorporated by reference.

The invention relates to a process for treating an organic solution comprising cyclohexanone oxime, cyclohexanone and an organic solvent.

Oximes can be produced in a process in which a buffered, aqueous reaction medium containing buffer acids or acidic salts, for example phosphate buffers, and buffer salts derived from these acids, is continuously recycled between a hydroxylammonium synthesis zone and an cyclohexanone oxime synthesis zone. In the hydroxylammonium synthesis zone hydroxylammonium may be formed by catalytic reduction of nitrate ions or nitric oxide with hydrogen. In the cyclohexanone oxime synthesis zone, hydroxylammonium formed in the hydroxylammonium synthesis zone may react with cyclohexanone to form cyclohexanone oxime. The cyclohexanone oxime can then be separated from the aqueous reaction medium which is recycled to the hydroxylammonium synthesis zone.

The net chemical reactions occurring during the process can be represented by the following equations:

1) Preparation of the hydroxylammonium:

2) Preparation of the oxime

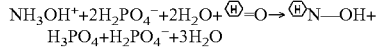

3) Supply of $HNO_3$ to make up the depletion of the source of nitrate ions after removal of the oxime formed

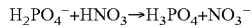

In the cyclohexanone oxime synthesis zone, cyclohexanone oxime may be prepared by countercurrently contacting an aqueous medium comprising hydroxylammonium in water with an organic medium comprising cyclohexanone dissolved in an organic solvent, e.g. toluene or benzene. An organic solution comprising the formed cyclohexanone oxime dissolved in organic solvent may be withdrawn from the reaction zone, and distilled to recover cyclohexanone oxime.

GB-A-1,138,750 discloses a process, wherein the conversion of cyclohexanone in the cyclohexanone oxime synthesis zone is incomplete, resulting in an organic solution comprising, besides cyclohexanone oxime and organic solvent, cyclohexanone. In said process the organic solution containing the residual cyclohexanone is fed to an after-reaction vessel to convert the residual cyclohexanone into cyclohexanone oxime by reaction with hydroxylammonium at an increased pH. After the conversion of the residual cyclohexanone in the after-reaction vessel, the organic solution is subjected to the distillation to recover the cyclohexanone oxime. This process is disadvantageous, since the after-reaction results in salt formation.

EP-A-5291 also describes a process wherein the conversion of cyclohexanone is incomplete, resulting in an organic solution comprising, cyclohexanone oxime, organic solvent (toluene) and cyclohexanone. In order to obviate the conversion of cyclohexanone in the after-reaction vessel, EP-A-5291 provides a process, wherein the cyclohexanone-containing organic solution is subjected to distillation. In a first step organic solvent is separated out as a (first) top product. The resulting bottom product is further distilled to obtain cyclohexanone oxime as a bottom product. As a result of this further distillation a (second) top product is obtained comprising cyclohexanone and organic solvent. Accordingly, the process of EP-A-5291 results in a first product comprising organic solvent, a second product comprising cyclohexanone, and a third product comprising cyclohexanone oxime.

In the process of EP-A-5291, the second product comprising cyclohexanone is not further used or treated. The distillation is carried out extensively, e.g. using a reflux or a three-column system, presumably to separate out as much of the cyclohexanone oxime as possible. Such extensive distillation has the disadvantage that it requires high investment and/or operational costs.

Goal of the invention is to provide a process wherein such extensive distillation and complete separation of cyclohexanone oxime is not necessary.

Accordingly, the invention provides a process for preparing cyclohexanone oxime, said process comprising: in a cyclohexanone oxime synthesis zone, reacting hydroxylammonium with cyclohexanone to form cyclohexanone oxime; distilling an organic solution comprising cyclohexanone oxime, cyclohexanone and an organic solvent to obtain (i) a first product comprising organic solvent, (ii) a second product comprising cyclohexanone and (iii) a third product comprising cyclohexanone oxime; and feeding the second product into said cyclohexanone oxime synthesis zone.

According to the invention complete separation of the cyclohexanone oxime by extensive distillation is not necessary. Cyclohexanone oxime that may be present in the second product, may be recovered from the cyclohexanone oxime synthesis zone together with cyclohexanone oxime formed in the cyclohexanone oxime synthesis zone.

The invention also provides preferred levels for feeding the second product into the cyclohexanone oxime synthesis zone. The preferred levels result in decreased concentrations of organic compounds, in particular of cyclohexanone and cyclohexanone oxime in the aqueous medium leaving the cyclohexanone oxime synthesis zone. A low sum concentration of cyclohexanone and cyclohexanone oxime in the aqueous medium leaving the cyclohexanone oxime synthesis zone has the advantage that, when the aqueous medium is recycled to a hydroxylammonium synthesis zone, the extent of catalyst poisoning in the hydroxylammonium synthesis zone decreases and/or that separation steps for removing said cyclohexanone oxime and/or cyclohexanone from the aqueous medium prior to recycling to a hydroxylammonium synthesis zone can be omitted and/or carried out to a lesser extent. Preferably, the process comprises feeding the second product to the cyclohexanone oxime synthesis such that the sum concentration of cyclohexanone and cyclohexanone oxime in the aqueous medium leaving the cyclohexanone oxime synthesis zone contains less than 20,000 ppm (2 wt. %, relative to the weight of the aqueous medium), preferably less than 5,000 ppm (0.5 wt. %), more preferably less than 1,000 ppm (0.1 wt. %), more preferably less than 500 ppm (0.05 wt. %), more preferably less than 200 ppm (0.02 wt. %).

The process according to the invention comprises reacting hydroxylammonium with cyclohexanone to form cyclohexanone oxime. Reaction is advantageously achieved by countercurrently contacting an aqueous medium with an organic medium in said cyclohexanone oxime synthesis zone, said aqueous medium containing hydroxylammonium, said organic medium comprising cyclohexanone and, preferably, organic solvent. Organic solvent may be fed into the cyclohexanone oxime synthesis zone in any suitable manner. The level at which the organic solvent is fed into the cyclohexanone oxime synthesis zone is, as used herein, referred to as feeding level for organic solvent. The organic solvent that is fed into the cyclohexanone oxime synthesis zone at the feeding level for organic solvent may be any suitable stream of organic solvent, preferably the first product.

Cyclohexanone to be reacted may be fed into the cyclohexanone oxime synthesis zone in any suitable manner. The level at which the cyclohexanone is fed into the cyclohexanone oxime synthesis zone is, as used herein, referred to as feeding level for cyclohexanone. The cyclohexanone that is fed to the cyclohexanone oxime synthesis zone at the feeding level for cyclohexanone may be any suitable stream of cyclohexanone, for instance a stream comprising at least 75 wt. %, preferably at least 90 wt. % of cyclohexanone. In an embodiment, the feeding level for cyclohexanone is downstream of the feeding level for organic solvent (seen in the direction of flow of the organic medium).

Cyclohexanone oxime formed by the reaction may be discharged from the cyclohexanone oxime synthesis zone in any suitable manner, for instance by discharging an organic product solution comprising cyclohexanone oxime and organic solvent from the cyclohexanone oxime synthesis zone. The level at which the organic product solution is discharged from the cyclohexanone oxime synthesis zone is, as used herein, referred to as discharge level for organic product solution. In an embodiment the discharge level for organic product solution is downstream of the feeding level for organic solvent. In an embodiment, the discharge level for organic product solution is downstream of the feeding level for cyclohexanone. In an embodiment, the discharge level for organic product solution is downstream of the feeding level for organic solvent and downstream of the feeding level for cyclohexanone.

As a cyclohexanone oxime synthesis zone any suitable countercurrent contact zone may be used in which the aqueous medium and organic medium are countercurrently contacted. The cyclohexanone oxime synthesis zone may comprise a first contact zone, in which the aqueous medium and the organic medium downstream of the feeding level for cyclohexanone and upstream of the discharge level for organic product solution are countercurrently contacted (seen in the flow direction of organic medium). As a first contact zone may be used any suitable type of counterflow reactors, for instance an extraction column, preferably a pulsed packed column or rotating disc reactors. It is also possible to use as a first contact zone a system comprising a number, preferably at least 3, e.g. 3 to 6, series-conneced reactors equipped with stirrers, each of these reactors also being provided with a liquid-liquid separator. These may also be referred to as mixer-settlers. The cyclohexanone oxime synthesis zone may also comprise a second contact zone, in which the aqueous medium and the organic medium downstream of the feeding level for organic solvent and upstream of the feeding level for cyclohexanone are countercurrently contacted (seen in the flow direction of the organic medium). As a second contact zone may be used any suitable type of counterflow reactors, for instance an extraction column, preferably a pulsed packed column or rotating disc reactors. It is also possible to use as a second contact zone a system comprising a number, preferably at least 3, e.g. 3 to 6, series-connected reactors equipped with stirrers, each of these reactors also being provided with a liquid-liquid separator.

Preferred embodiments in which the second product is fed into the cyclohexanone oxime synthesis zone at preferred levels are described hereinafter. The preferred levels have the advantage that the sum concentration of cyclohexanone and cyclohexanone oxime in the aqueous medium leaving the cyclohexanone oxime synthesis zone is decreased. In the entire description and claims, the terms downstream and upstream are defined relative to the flow direction of the organic medium.

In a preferred embodiment for achieving a low sum concentration of cyclohexanone and cyclohexanone oxime in the aqueous medium leaving the cyclohexanone oxime synthesis zone, the process according the invention comprises feeding the second product into the cyclohexanone oxime synthesis zone at a level downstream of the feeding level for organic solvent. More preferably, the second product is fed into the cyclohexanone oxime synthesis zone at the feeding level for cyclohexanone or downstream of the feeding level for cyclohexanone. This is found to result in a further decrease of the sum concentration of cyclohexanone and cyclohexanone oxime in the aqueous medium leaving the cyclohexanone oxime synthesis zone. Feeding the second product into the cyclohexanone oxime synthesis zone at the feeding level for cyclohexanone may for instance be carried out by feeding cyclohexanone, e.g. as a stream of cyclohexanone comprising for instance at least 75 wt. % of cyclohexanone, preferably at least 90 wt. % of cyclohexanone, and the second product separately into the cyclohexanone oxime synthesis zone at the feeding level for cyclohexanone or by mixing cyclohexanone, e.g. a stream of cyclohexanone comprising for instance at least 75 wt. % of cyclohexanone, preferably at least 90 wt. % of cyclohexanone with the second product, and feeding the resulting mixture into the cyclohexanone oxime synthesis zone at the feeding level for cyclohexanone. In a preferred embodiment, the process comprises feeding the second product upstream of the discharge level for organic product solution (seen in the direction of flow of the organic medium). This facilitates the reaction of the cyclohexanone supplied to the cyclohexanone oxime synthesis zone via the second product.

In a preferred embodiment, the aqueous medium and organic medium present downstream of the feeding level for cyclohexanone and upstream of the discharge level for organic product solution have a sum volume of V, the process comprising feeding the second product into the cyclohexanone oxime synthesis zone at a level such that the aqueous medium and the organic medium present downstream of the feeding level for cyclohexanone and upstream of the level at which the second product is fed into cyclohexanone oxime synthesis zone have a sum volume of at least $V/10$, preferably of at least $V/5$. This facilitates the decrease of the sum concentration of cyclohexanone and cyclohexanone oxime in the aqueous medium leaving the cyclohexanone oxime synthesis zone. As used herein sum volume refers to the volume of the aqueous medium and the organic medium. Preferably, the process comprises feeding the second product into the cyclohexanone oxime synthesis zone at a level such that the aqueous medium and the organic medium present downstream of the feeding level for cyclohexanone and upstream of the level at which the second product is fed into cyclohexanone oxime synthesis zone have a sum volume of less than $9*V/10$, preferably of less than $4*V/5$. This facilitates the reaction of the cyclohexanone supplied to the cyclohexanone oxime synthesis zone via the second product.

In a preferred embodiment, the process comprises countercurrently contacting the aqueous medium and the organic medium present downstream of the feeding level for cyclohexanone and upstream of the discharge level for organic product solution in a column or in series-connected columns, said column or said series-connected columns having a total column length L, and feeding the second product into said column or series-connected columns at a distance of at least L/10 measured from said feeding level for cyclohexanone. This facilitates the decrease of the sum concentration of cyclohexanone and cyclohexanone oxime in the aqueous medium leaving the cyclohexanone oxime synthesis zone. As used herein the total column length L refers to the column length if the aqueous medium and the organic medium downstream of the feeding level for cyclohexanone and upstream of the discharge level for organic product solution are contacted in one column, and to the sum length of columns of the series-connected columns if the aqueous medium and the organic medium downstream of the feeding level for cyclohexanone and upstream of the discharge level for organic product solution are countercurrently contacted in series-connected columns. Preferably, the process comprises feeding the second product into the column or series-connected columns at a distance of less than 9*L/10, more preferably a distance of less than 4*L/5, measured from the feeding level for cyclohexanone. This facilitates the reaction of the cyclohexanone supplied to the cyclohexanone oxime synthesis zone via the second product.

In a preferred embodiment, the process comprises countercurrently contacting the aqueous medium and the organic medium present downstream of the feeding level for cyclohexanone and upstream of the discharge level for organic product solution in a number (m) of series-connected mixer-settlers; and feeding the second product into to the second or higher-numbered mixer-settler counted from the feeding level for cyclohexanone. This facilitates the decrease of the sum concentration of cyclohexanone and cyclohexanone oxime in the aqueous medium leaving the cyclohexanone oxime synthesis zone. Preferably, the process comprises feeding the second product to the m, m−1, or lower-numbered mixer-settler, counted from the feeding level for cyclohexanone. This facilitates the reaction of the cyclohexanone supplied to the cyclohexanone oxime synthesis zone via the second product.

The organic solution may be any organic solution comprising cyclohexanone oxime, cyclohexanone and an organic solvent. Preferably the process according to the invention comprises withdrawing the organic solution from a cyclohexanone oxime synthesis zone. More preferably, the process according to the invention comprises withdrawing the organic solution from the cyclohexanone oxime synthesis zone to which the second product is fed. The concentration of cyclohexanone in the organic solution may be higher than 0.1 wt. %, preferably higher than 0.5 wt. %, most preferably higher than 1 wt. %. The concentration of cyclohexanone in the organic solution may be lower than 10 wt. %, preferably lower than 5 wt. %. The concentration of cyclohexanone oxime in the organic solution may be higher than 5 wt. %, preferably higher than 10 wt. %, more preferably higher than 25 wt. %, and may be lower than 60 wt. %, preferably lower than 50 wt. %. The concentration of organic solvent in the organic solution may be higher than 40 wt. %, preferably higher than 50 wt. %, and may be lower than 95 wt. %, preferably lower than 90 wt. %. Preferably the organic solution is an organic product solution comprising organic solvent, cyclohexanone oxime and cyclohexanone, said organic product solution being discharged from a or from the cyclohexanone oxime synthesis zone, preferably at the discharge level for organic product solution. The preferred concentrations for the organic solvent, cyclohexanone oxime and cyclohexanone in the organic solution are also preferred concentrations for the organic product solution.

The distillation according to the invention results in a first product comprising organic solvent, a second product comprising cyclohexanone and a third product comprising cyclohexanone oxime. The distillation can be effected in any suitable manner, and preferably involves obtaining a first product enriched in organic solvent, a second product enriched in cyclohexanone and third product enriched in cyclohexanone oxime. As used herein, a first product enriched in organic solvent is understood to mean that the concentration of organic solvent in the first product is higher than in the concentration of organic solvent in the organic solution. As used herein, a second product enriched in cyclohexanone is understood to mean that the concentration of cyclohexanone in the second product is higher than the concentration of cyclohexanone in the organic solution. As used herein, a third product enriched in cyclohexanone oxime is understood to mean that the concentration of cyclohexanone oxime in the third product is higher than the concentration of cyclohexanone oxime in the organic solution.

In a preferred embodiment, the second product is obtained as a distillate (overhead product). Preferably, the process comprises distilling the organic solution to obtain the first product as a distillate; distilling the remaining bottom product to obtain the second product as a distillate and the third product as a bottom product. Preferably, the distillation of the organic solution to obtain the first product as a distillate is carried out at a temperature of between 35 and 80° C., more preferably between 50 and 70° C. Preferably, the distillation to obtain the first product as a distillate is effected at a pressure of between 0.006 and 0.4 MPa and more preferably between 0.012 and 0.025 MPa. The first product may for instance comprise at least 98 wt. % of organic solvent, preferably at least 99 wt. % of organic solvent, more preferably at least 99.5 wt. % of organic solvent, most preferably at least 99.9 wt. % of organic solvent (with respect to the weight of the first product). The first product is preferably recycled to a or to the cyclohexanone oxime synthesis zone, preferably at the feeding level for organic solvent. Preferably, the distillation of the remaining bottom product to obtain the second product as a distillate and the third product as a bottom product is carried out at a temperature of between 70 and 115° C., more preferably between 85 and 100° C. Preferably, the distillation of the remaining bottom product to obtain the second product as a distillate and the third product as a bottom product is carried out at a pressure of between 0.010 and 0.020 MPa. Preferably, the third product comprises at least 95 wt. % of cyclohexanone oxime, more preferably at least 98 wt. % of cyclohexanone oxime, most preferably at least 99 wt. % of cyclohexanone oxime (with respect to the weight of the third product). As used herein, the temperature refers to the temperature in the top of a column in which the distillation is effected. As used herein, the pressure refers to the pressure in the top of a column in which the distillation is effected.

According to the invention a second product is obtained containing cyclohexanone and which preferably also contains cyclohexanone oxime. Preferably, the weight ratio cyclohexanone oxime/cyclohexanone in the top product is higher than 0.1, preferably higher than 0.2, more preferably higher than 0.3, in particular higher than 0.4, more in particular higher than 0.5. An increased ratio has the advantage that the distillation can be effected in a simpler way. The ratio cyclohexanone oxime/cyclohexanone in the top product is for instance less than 100. The second product may comprise organic solvent, for instance more than 10 wt. %, preferably more than 25 wt. %, more preferably more than 50 wt. %, for instance less than 95 wt. %, preferably less than 90 wt. %. Preferably, the sum concentration of cyclohexanone and cyclohexanone oxime in the top product is higher than 5 wt. %, more preferably higher than 10 wt. %. Preferably, the sum concentration of cyclohexanone and cyclohexanone oxime in the second product is less than 75 wt. %, more preferably less than 50 wt. %. All weight percentages are given with respect to the weight of the second product.

The distillation may be carried out using any suitable column or combination of columns. Preferably, the distillation is carried out using two or three columns, most preferably two columns. Preferably, the process comprises, preferably in a system comprising two columns, distilling the organic solution in a first column to obtain the first product as a distillate; and feeding the remaining bottom product to the top of a distillation column or to a column without a rectifying section. This is a simpler way of distilling which is made possible by the process according to the invention.

Any suitable aqueous medium containing hydroxylammonium may be fed to the cyclohexanone oxime synthesis zone. The concentration hydroxylammonium in the aqueous reaction medium entering (fed to) the cyclohexanone oxime synthesis zone may have any suitable value, for instance higher than 0.7 mol/l, preferably higher than 1.0 mol/l, and may be below 2.5 mol/l.

We found that the process according to the invention has additional advantages in a preferred embodiment wherein the ratio $f_h/f_c<1.00$, more preferably <0.99, more preferably less than 0.98, wherein $f_h$ represents the molar quantity of hydroxylammonium fed to the cyclohexanone oxime synthesis zone per unit of time (in mol/s), and $f_c$ represents the molar quantity of cyclohexanone fed to the cyclohexanone oxime synthesis zone per unit of time (in mol/s). Decreasing this ratio has the advantage that the concentration organic compounds, in particular cyclohexanone and cyclohexanone oxime in the aqueous medium leaving the cyclohexanone oxime synthesis zone is decreased. An organic product solution containing unconverted cyclohexanone obtained by the embodiment wherein $f_h/f_c<1.00$ may advantageously be distilled by the process according to the invention. There is no specific lower limit for the ratio $f_h/f_c$. The ratio $f_h/f_c$ is generally higher than 0.5, preferably higher than 0.7, more preferably higher than 0.8.

Preferably, the aqueous medium contains phospate. Preferably, the aqueous medium is an acidic, buffered medium. The phosphate concentration in the aqueous medium entering (fed to) the cyclohexanone oxime synthesis zone is higher than 2.0 mol/l, preferably higher than 2.5 mol/l, more preferably higher than 3.0 mol/l, in particular higher than 3.3 mol/l, more in particular higher than 3.5 mol/l, most preferably higher than 3.7 mol/l. We have found that increasing the phosphate concentration in the aqueous medium entering the cyclohexanone oxime synthesis zone is advantageous, since it results in a decrease of the concentration of organic contaminants in the aqueous medium exiting the cyclohexanone oxime synthesis zone. The phosphate concentration in the aqueous medium entering the cyclohexanone oxime synthesis zone may be lower than 8 mol/l, preferably lower than 5 mol/l, more preferably lower than 4.5 mol/l. As used herein, the phosphate concentration denotes the sum concentration of all phosphates, irrespective of the form in which they are present, expressed in mol per liter of aqueous reaction reaction medium. Preferably, the phosphates are present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof. The aqueous medium may contain ammonium ($NH_4^+$), for instance formed as a by-product in the synthesis of hydroxylammonium. Preferably, in the aqueous medium entering the cyclohexanone oxime synthesis zone, the ratio $c(NH_4^+)/c(phosphate)$ is between 0.1 and 3, more preferably between 0.2 and 2, most preferably between 0.5 and 1.5, wherein $c(NH_4^+)$ represents the concentration of $NH_4^+$ in mol/l and c(phosphate) represents the phosphate concentration in mol/l. The aqueous medium entering the cyclohexanone oxime synthesis zone may contain nitrate ($NO_3^-$). Preferably, in the aqueous medium entering the cyclohexanone oxime synthesis zone, the $c(NO_3^-)/c(phosphate)$ is between 0.05 and 1, more preferably between 0.1 and 0.5, wherein $c(NO_3^-)$ represents the concentration of $NO_3^-$ in mol/l and c(phosphate) represents the phosphate concentration in mol/l. Preferably, the aqueous medium which is fed to the cyclohexanone oxime synthesis zone has a pH of between 1 an 6, more preferably between 1.5 and 4.

The cyclohexanone oxime synthesis zone may be operated at a temperature ranging from 40 to 150° C. and at atmospheric, sub-atmospheric, or elevated pressures, preferably between 0.05 and 0.5 MPa, more preferably between 0.1 and 0.2 MPa, most preferably between 0.1 and 0.15 MPa.

Any suitable organic solvent may be used. Preferably, the organic solvent is selected from the group consisting of benzene, toluene, xylene, methylcyclopentane, cyclohexane and mixtures thereof. Most preferably, the organic solvent is toluene.

In a preferred embodiment, the process comprises passing the aqueous medium leaving the cyclohexanone oxime synthesis zone to a hydroxylammonium synthesis zone, and from the hydroxylammonium synthesis zone back to the cyclohexanone oxime synthesis zone. In the hydroxylammonium synthesis zone hydroxylammonium may be formed by catalytic reduction of nitrate or nitrogen oxide with hydrogen. Preferably, the catalyst is a palladium containing catalyst, for instance a palladium or a palladium-platinum catalyst, present on a support, such as for instance carbon or alumina support.

In a preferred embodiment, the process comprises separating, by stripping, organic solvent, cyclohexanone, and/or cyclohexanone oxime, from the aqueous medium leaving the cyclohexanone oxime synthesis zone. Preferably, said stripping is carried out prior to recycling the aqueous medium to a hydroxylammonium synthesis zone. This has the advantage that poisoning of the catalyst in a hydroxylammonium synthesis zone is avoided or minimized. The stripping process described in U.S. Pat. No. 3,940,442 may for instance be used. It is preferred that the sum concentration of cyclohexanone and cyclohexanone in the aqueous medium entering the hydroxylammonium synthesis zone is not more than 0.02 wt. % (200 ppm), more preferably not more than 0.005 wt. %, in particular not more than 0.002 wt. %, more in particular not more than 0.001 wt. % and most preferably not more than 0.0002 wt. % (relative to the weight of the aqueous medium). The stripping may also include separation of water from the aqueous medium. Preferably, the separated organic solvent, cyclohexanone and/or cyclohexanone oxime to the cyclohexanone oxime synthesis zone are recycled to the cyclohexanone oxime synthesis zone.

Preferably, the process is a continuous process.

Figure 1:
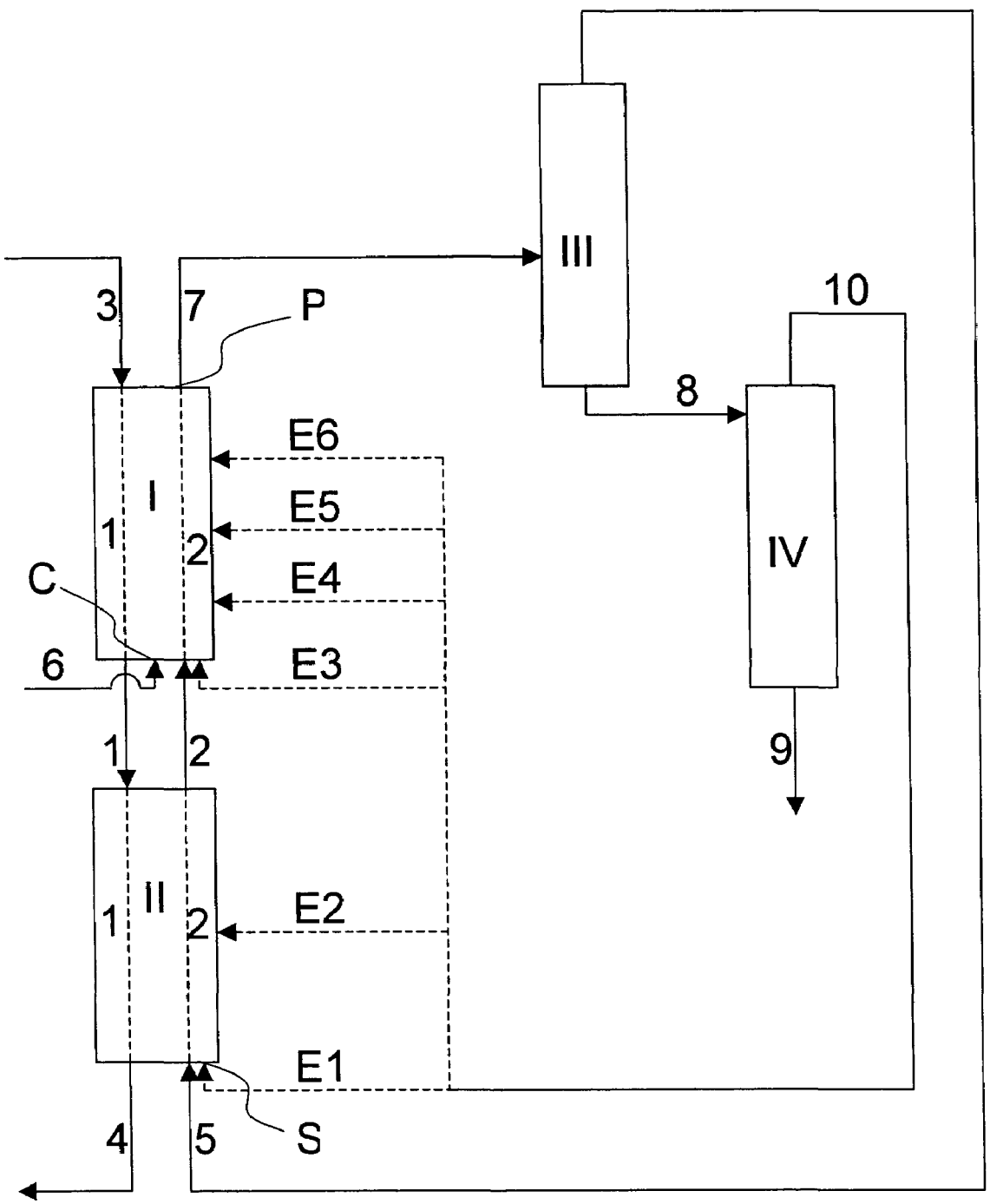
FIG. 1 represents a schematic overview of a process for preparing cyclohexanone oxime.

A preferred embodiment of the process according to the invention is schematically illustrated in FIG. 1. In this embodiment, the cyclohexanone oxime synthesis zone comprises a first contact zone (I), and a second contact zone (II).

In the cyclohexanone oxime synthesis zone an aqueous medium containing hydroxylammonium in water is countercurrently contacted with an organic medium comprising cyclohexanone and organic solvent. The aqueous medium and organic medium in the cyclohexanone oxime synthesis zone are represented by lines (1) and (2) respectively. The aqueous medium is supplied to the first contact zone (I) of the cyclohexanone oxime synthesis zone via line (3) and is discharged from the second contact zone (II) of the cyclohexanone oxime synthesis zone via line (4). At feeding level for organic solvent (S), organic solvent, preferably toluene, is fed into the cyclohexanone oxime synthesis zone via line (5). At feeding level for cyclohexanone (C), a stream of cyclohexanone is fed into the cyclohexanone oxime synthesis zone via line (6). The feeding level for cyclohexanone (C) is downstream of the feeding level for organic solvent (S), seen in the direction of flow of the organic medium. In the cyclohexanone oxime synthesis zone, cyclohexanone reacts with hydroxylammonium to form cyclohexanone oxime. An organic product solution comprising cyclohexanone oxime and cyclohexanone dissolved in organic solvent (toluene) is discharged from the cyclohexanone oxime synthesis zone via line (7) at discharge level for organic product solution (P). The organic product solution is, preferably after having been washed with water or an aqueous solution, fed to distillation column (III). In distillation column (III) the organic solution distilled to obtain the first product comprising organic solvent (toluene) as a distillate. The first product is fed to the cyclohexanone oxime synthesis zone at the feeding level for organic solvent (S). The remaining bottom product comprising cyclohexanone oxime, cyclohexanone, and organic solvent (toluene) leaves the first distillation column via line (8), and is fed to the top of distillation column (IV). In distillation column (IV), the second product comprising cyclohexanone is obtained as a distillate and the third product comprising cyclohexanone oxime is obtained as a bottom product. The third product leaves distillation column (IV) via line (9). The second product leaves the distillation column (IV) via line (10), and is fed into the cyclohexanone oxime synthesis zone.

The following specific examples are to be construed as merely illustrative, and not limitative, of the remainder of the disclosure.

EXAMPLES

Example I

This example is carried out using the set-up as illustrated in FIG. 1. The cyclohexanone oxime synthesis zone is formed by two pulsed packed columns (PPC's), the first PPC having a diameter of 1200 mm and a height of 13200 mm, the second PPC having a diameter of 1075 mm and a height of 11000 mm. The first PPC is operated at a temperature of 50° C. The second PPC is operated at a temperature of 70° C. An aqueous medium (hydroxylammonium=1.6 mol/l, $H^+$=0.7 mol/l (pH=1.9), $H_2PO_4^-$=3.9 mol/l, $NH_4^+$=3.0 mol/l, $NO_3^-$=1.4 mol/l) is fed to the top of the first PPC (via line 3), the flow rate being 23 $m^3$ per hour. To the bottom of the first PPC were fed cyclohexanone as well as the organic medium leaving the second PPC. The organic product solution leaving the top of the first PPC (via line 7) is fed to a first column (packed column having a stripping section and a rectifying section). In the first distillation column, the pressure in the top is 0.16 bar. Toluene having 99.9 wt. % purity leaves the top of the first distillation column. Toluene leaving the top of the first distillation column is recycled to the bottom of the second PPC. The bottom product of the first distillation column is fed to the top a second column (packed column). The pressure in the top of the second distillation column is 0.12 bar. Cyclohexanone oxime leaves the bottom of the second distillation column. The top product (for composition see table 1) of the second distillation column (=second product) is fed to the bottom of the second PPC (E1). The sum concentration of cyclohexanone oxime and cyclohexanone in the aqueous medium leaving the bottom of the second PPC is 13000 ppm.

Example II

Example I is repeated with the difference that the top product of the second distillation column is fed to the middle (50% of the height) of the second PPC (position E2 in FIG. 1). The sum concentration of cyclohexanone oxime and cyclohexanone in the aqueous medium leaving the bottom of the second PPC is 4300 ppm. This example shows that feeding the top product (second product) downstream of the level where the organic solvent is fed into the cyclohexanone oxime synthesis zone results in a decrease of the sum concentration of cyclohexanone and cyclohexanone oxim in the aqueous medium leaving the cyclohexanone oxime synthesis zone.

Example III

Example I is repeated with the difference that the top product of the second distillation column is, like the cylcohexanone, fed to the bottom of the first PPC (position E3 in FIG. 1). The sum concentration of cyclohexanone oxime and cyclohexanone in the aqueous medium leaving the bottom of the second PPC is 800 ppm. This example shows that feeding the top product (second product) to the cyclohexanone oxime synthesis zone at the same level as cyclohexanone, results in a further decrease of the sum concentration of cyclohexanone and cyclohexanone oxim in the aqueous medium leaving the cyclohexanone oxime synthesis zone.

Example IV

Example I is repeated with the difference that the top product of the second distillation column into the first PPC at 20% of the height of the column (position E4 in FIG. 1).

The sum concentration of cyclohexanone oxime and cyclohexanone in the aqueous medium leaving the bottom of the second PPC is 180 ppm. This example shows that feeding the top product (second product) to the cyclohexanone oxime synthesis zone downstream of the level where cyclohexanone is fed to the cyclohexanone oxime synthesis zone, results in a further decrease of the sum concentration of cyclohexanone and cyclohexanone oxim in the aqueous medium leaving the cyclohexanone oxime synthesis zone.

Example V

Example I is repeated with the difference that the top product of the second distillation column ito the first PPC at 50% of the height of the column (position E5 in FIG. 1).

The sum concentration of cyclohexanone oxime and cyclohexanone in the aqueous medium leaving the bottom of the second PPC is 60 ppm. This example shows that feeding the top product (second product) further downstream results in a further decrease of the sum concentration of cyclohexanone and cyclohexanone oxim in the aqueous medium leaving the cyclohexanone oxime synthesis zone.

Example VI

Example I is repeated with the difference that the top product of the second distillation column into the first PPC at 80% of the height of the column (position E6 in FIG. 1). The sum concentration of cyclohexanone oxime and cyclohexanone in the aqueous medium leaving the bottom of the second PPC is 45 ppm. This example shows that feeding the top product (second product) further downstream results in a further decrease of the sum concentration of cyclohexanone and cyclohexanone oxim in the aqueous medium leaving the cyclohexanone oxime synthesis zone.

TABLE 1 overview of examples I to VI

|  | ex. I | ex. II | ex. III | ex. IV | ex. V | ex. VI |
|---|---|---|---|---|---|---|
| Cyclohexanone |  |  |  |  |  |  |
| flow rate ($10^3$ kg/hr) product solution | 3.5 | 3.3 | 3.4 | 3.5 | 3.6 | 3.6 |
| flow rate ($10^3$ kg/hr) | 12.2 | 12.2 | 12.9 | 13.3 | 13.6 | 13.9 |
| anone conc. (wt. %) | 1.4 | 1.1 | 1.1 | 1.2 | 1.5 | 1.9 |
| oxime conc. (wt. %) | 35.0 | 35.0 | 35.0 | 34.9 | 35.0 | 34.0 |
| toluene con. (wt. %) second product | 63.6 | 63.9 | 63.9 | 63.9 | 63.5 | 64.1 |
| flow rate ($10^3$ kg/hr) | 2.5 | 2.6 | 3.0 | 3.3 | 3.4 | 3.7 |
| anone conc. (wt. %) | 5.3 | 5.3 | 4.8 | 4.7 | 5.9 | 6.8 |
| oxime conc. (wt. %) | 22.8 | 22.6 | 19.3 | 17.8 | 16.6 | 15.4 |
| toluene con. (wt. %) aqueous medium | 71.9 | 72.1 | 75.9 | 77.5 | 77.5 | 77.8 |
| anone + oxime (ppm) | 13000 | 4300 | 800 | 180 | 60 | 45 |

The invention claimed is:

1. Process for preparing cyclohexanone oxime which comprises:
    (a) feeding organic solvent into a cyclohexanone oxime synthesis zone at a feeding level for organic solvent, and countercurrently contacting an aqueous medium which comprises hydroxylammonium with an organic medium which comprises cyclohexanone;
    (b) reacting said hydroxylammonium with said cyclohexanone to form cyclohexanone oxime;
    (c) distilling an organic solution comprising cyclohexanone oxime, cyclohexanone and the organic solvent to obtain (i) a first product comprising organic solvent, (ii) a second product comprising cyclohexanone oxime and cyclohexanone at a weight ratio of cyclohexanone oxime/cyclohexanone of greater than 0.5, and (iii) a third product comprising cyclohexanone oxime; and
    (d) feeding the second product into said cyclohexanone oxime synthesis zone at a level downstream of the feeding level for organic solvent in relation to a flow direction the organic medium.

2. Process according to claim 1, wherein the process further comprises:
    feeding cyclohexanone into the cyclohexanone oxime synthesis zone at a feeding level for cyclohexanone, said feeding level for cyclohexanone being downstream of the feeding level for organic solvent in relation to the flow direction of the organic medium; and
    feeding said second product into the cyclohexanone oxime synthesis zone at said feeding level for cyclohexanone or downstream of the feeding level for cyclohexanone in relation to the flow direction of the organic medium.

3. Process according to claim 1, wherein the process further comprises discharging an organic product solution which comprises cyclohexanone oxime and organic solvent from said cyclohexanone oxime synthesis zone at a discharge level for organic product solution, said discharge level for organic product solution being downstream of the feeding level for cyclohexanone in relation to the flow direction of the organic medium.

4. Process according to claim 3, wherein the process further comprises feeding the second product upstream of the discharge level for organic product solution in relation to the flow direction of the organic medium.

5. Process according to claim 3, wherein the aqueous medium and organic medium present between the feeding level for cyclohexanone and the discharge level for organic product solution have a sum volume of V, and wherein the process comprises feeding the second product into the cyclohexanone oxime synthesis zone at a level such that the aqueous medium and the organic medium present between the feeding level for cyclohexanone and the level at which the second product is fed into cyclohexanone oxime synthesis zone have a sum volume of at least V/10.

6. Process according to claim 3, wherein the process further comprises:
    countercurrently contacting the aqueous medium and the organic medium present between the feeding level for cyclohexanone and the discharge level for organic product solution in a column or in series-connected columns, said column or said series-connected columns having a total column length L; and
    feeding the second product into said column or series-connected columns at a distance of at least L/10 measured from said feeding level for cyclohexanone.

7. Process according to claim 3, wherein the process further comprises:
    countercurrently contacting the aqueous medium and the organic medium present between the feeding level for cyclohexanone and the discharge level for organic product solution in a number of series-connected mixer-settlers; and feeding the second product into the second or higher-numbered mixer-settler counted from the feeding level for cyclohexanone.

8. Process according to claim 3, wherein said organic product solution is said organic solution.

9. Process according to claim 1, wherein the process comprises feeding the second product into the cyclohexanone oxime synthesis zone such that the sum concentration of cyclohexanone and cyclohexanone oxime in the aqueous medium leaving the cyclohexanone oxime synthesis zone is less than 20,000 ppm (2 wt. %).

10. Process according to claim 1, wherein said feeding of organic solvent into the cyclohexanone oxime synthesis zone at the feeding level for organic solvent is effected by feeding the first product into the cyclohexanone oxime synthesis zone at the feeding level for organic solvent.

11. Process according to claim 1, wherein said second product contains cyclohexanone oxime.

12. Process according to claim 1, wherein the process comprises distilling the organic solution to obtain the first product as a distillate; distilling the remaining bottom product to obtain the second product as a distillate and the third product as a bottom product.

13. Process according to claim 1, wherein the process comprises withdrawing said organic solution from the cyclohexanone oxime synthesis zone.

14. Process according to claim 1, wherein the ratio $f_n/f_c<1.00$, wherein $f_n$ represents the molar quantity of hydroxylammonium fed to the cyclohexanone oxime synthesis zone per unit of time (in mol/s), and $f_c$ represents the molar quantity of cyclohexanone fed to the cyclohexanone oxime synthesis zone per unit of time (in mol/s).

15. Process according to claim 1, wherein the organic solvent is selected from the group consisting of benzene, toluene, xylene, methylcyclopentane, cyclohexane and mixtures thereof.

16. Process according to claim 15, wherein the organic solvent is toluene.

17. Process according to claim 1, wherein the aqueous medium is an acidic medium buffered with phosphate.

18. Process according to claim 1, wherein the sum concentration of cyclohexanone and cyclohexanone oxime in the aqueous medium leaving the cyclohexanone oxime synthesis zone is less than 5,000 ppm (0.5 wt. %).

19. Process according to claim 1, wherein the sum concentration of cyclohexanone and cyclohexanone oxime in the aqueous medium leaving the cyclohexanone oxime synthesis zone is less than 1,000 ppm (0.1 wt. %).

20. Process according to claim 1, wherein the sum concentration of cyclohexanone and cyclohexanone oxime in the aqueous medium leaving the cyclohexanone oxime synthesis zone is less than 500 ppm (0.05 wt. %).

21. Process according to claim 1, wherein the sum concentration of cyclohexanone and cyclohexanone oxime in the aqueous medium leaving the cyclohexanone oxime synthesis zone is less than 200 ppm (0.02 wt. %).

22. Process according to claim 1, wherein the weight ratio cyclohexanone oxime/cyclohexanone in the second product is between about 2.3 to 4.3.

* * * * *